United States Patent
Varis

(10) Patent No.: US 6,254,551 B1
(45) Date of Patent: Jul. 3, 2001

(54) APPARATUS FOR MONITORING A MECHANICALLY TRANSMITTED SIGNAL BASED ON THE ORGANS OR VITAL FUNCTIONS AND FOR PROCESSING THE RESULTS

(75) Inventor: Reijo Varis, Helsinki (FI)

(73) Assignee: Instrumentarium Corp., Helsinki (FI)

(*) Notice: Subject to any disclaimer, the term of this patent is extended or adjusted under 35 U.S.C. 154(b) by 0 days.

(21) Appl. No.: 09/355,576

(22) PCT Filed: Feb. 5, 1998

(86) PCT No.: PCT/FI98/00107

§ 371 Date: Jul. 29, 1999

§ 102(e) Date: Jul. 29, 1999

(87) PCT Pub. No.: WO98/34540

PCT Pub. Date: Aug. 13, 1998

(30) Foreign Application Priority Data

Feb. 5, 1997 (FI) .......................................... 970491
Feb. 7, 1997 (FI) .......................................... 970537

(51) Int. Cl.⁷ .................................................. A61B 5/103
(52) U.S. Cl. ............................................ 600/595; 600/534
(58) Field of Search .................................. 600/534, 535, 600/538, 546, 390, 391, 587, 595

(56) References Cited

U.S. PATENT DOCUMENTS

| 3,727,606 | 4/1973 | Sielaff . |
|---|---|---|
| 4,474,185 | 10/1984 | Diamond . |
| 4,657,026 | 4/1987 | Tagg . |
| 4,823,804 | 4/1989 | Ghislaine et al. . |
| 4,909,260 | 3/1990 | Salem et al. . |
| 4,958,638 | 9/1990 | Sharpe et al. . |
| 5,394,882 | * 3/1995 | Mawhinney ......................... 600/534 |
| 5,454,376 | * 10/1995 | Stephens et al. ..................... 600/534 |
| 5,511,553 | 4/1996 | Segalowitz . |
| 5,515,865 | 5/1996 | Scanlon . |

FOREIGN PATENT DOCUMENTS

| 44 37 538 | 5/1995 | (DE) . |
|---|---|---|
| 934012 | 3/1995 | (FI) . |
| 96/03075 | 2/1996 | (FR) . |
| 86/04497 | 8/1986 | (WO) . |
| 96/36279 | 11/1996 | (WO) . |

* cited by examiner

Primary Examiner—John P. Lacyk
Assistant Examiner—Pamela Wingood
(74) Attorney, Agent, or Firm—Andrus, Sceales, Starke & Sawall, LLP

(57) ABSTRACT

The invention relates to an apparatus for monitoring a mechanically transmitted signal based on the organs or vital functions and for processing the results, the apparatus comprising a measuring sensor arrangement (10) comprising one or more measuring sensors (1) and signal processing means (2; 2, 3, 4) for processing the sensor signal(s), transmission means (5; 5a, 5b) for transmitting the signal generated by the sensor arrangement (10), a data collecting device (6) for receiving and storing the signal transmitted by the transmission means, means (7) for processing the signal stored by the data collecting device (6) and a display or output device (8) for presenting the results. In accordance with the invention the measuring sensor arrangement (10) is arranged to produce the signal spectra based on a plurality of vital functions as a single composite signal spectrum, and the means (7) for processing the information stored by the data collecting device (6) comprise processing software for dividing the signal spectrum generated by the measuring sensor arrangement into a plurality of partial spectra of different physiological origins.

15 Claims, 5 Drawing Sheets

APPARATUS FOR MONITORING A MECHANICALLY TRANSMITTED SIGNAL BASED ON THE ORGANS OR VITAL FUNCTIONS AND FOR PROCESSING THE RESULTS

FIELD OF THE INVENTION

This invention relates to an apparatus for monitoring a mechanically transmitted signal based on the organs or vital functions and for processing the results, the apparatus comprising a measuring sensor arrangement comprising one or more measuring sensors and signal processing means for processing sensor signal(s), transmission means for transmitting the signal generated by the measuring sensor arrangement, a data collecting device for receiving and storing the signal transmitted by the transmission means, means for processing the signal stored in the data collecting device and a display or output device for presenting the results of processing.

Apparatuses of the type described above are known, for instance, from WO 86/04497 and German Patent 42 29 073 A1. By means of the apparatus known from WO 86/04497 respiration rate, heartbeat rate and total body movement can be monitored, and on the basis of these facts the amount of calories consumed can be determined. Thus the apparatus is mainly suitable for fitness training and rehabilitation. A strain-gage sensor that is arranged on the band closely fitted around the chest is used as a sensor in the apparatus.

DISCLOSURE OF THE INVENTION

The aim of the present invention is to bring about an apparatus by means of which vital functions can be monitored in a most versatile and accurate manner. This is achieved with the apparatus of the invention, the apparatus being characterized in that the measuring sensor arrangement is arranged to produce signal spectra based on a plurality of vital functions as a single composite signal spectrum, and the means for processing data, stored by the data collecting device, comprise processing software for dividing the signal spectrum generated by the measuring sensor arrangement into a plurality of partial spectra of different physiological origins. Thus for instance, as regards the function of the heart, it is not primarily the heartbeat rate that is monitored by means of the apparatus of the invention, but a graph corresponding to an electrocardiogram is produced, which also shows dysfunctions of the heart, if any. Likewise, as regards the function of the respiratory organs, a partial spectrum representing it discloses coughs, snore and other similar respiratory functions, in addition to respiration rate.

In accordance with a first embodiment of the invention a sensor arrangement comprising at least one of the following sensor types: capacitive acceleration transducer, EMF diaphragm sensor and strain-gage sensor, and perhaps most preferably one of each, is arranged to fit onto the user's chest without skin contact.

In accordance with a second embodiment of the invention the sensor arrangement is arranged in connection with a cushion to be placed under the user, the cushion being filled at least partly with fluid medium, and the sensor arrangement comprises a sensor responsive to pressure and communicating with the interior of the cushion, the sensor being preferably a capacitive pressure sensor based on silicon technology.

In accordance with the invention, the composite signal spectrum generated by the sensor arrangement comprises said signals based on a plurality of different vital functions as a single combined signal. Thus the sensor arrangement generates a signal in which all the signals of different origins are incorporated in one signal spectrum. If the sensor arrangement is incorporated in a band fitted onto the user's chest, it may preferably comprise an acceleration transducer, a strain-gage sensor and an EMF diaphragm sensor. The capacitive acceleration transducer with high sensitivity both at low and high frequencies collects information on several different factors, such as movement, position and heart beat of a human being. On the other hand, from the EMF diaphragm sensor, whose electrical conductivity changes in response to pressure, information is obtained both on heart beat and respiration. The straingage sensor for its part gives information mainly on respiration. Particularly with regard to respiration, various coughs and even minor vibrations, such as rate of lungs or bronchi or a similar noise audible by means of a stethoscope, can be detected. The sensor arrangement also reacts to a variety of other functions, such as speech and blowing of the nose.

When separate sensors are used for sensing various physiological parameters, it is possible to mix these signals into one signal as indicated above, but it is not absolutely necessary, since the readings of different sensors can be read sequentially as a time-division signal by means of signal processing means incorporated in the sensor arrangement. The sampling frequency of different sensors is naturally so great that the signal of each sensor can be separated on a time-division basis from the composite signal in full correspondence with a continuously measured signal.

A significant advantage of the apparatus of the invention is that despite accurate measurement results the measuring sensor arrangement can be arranged to fit onto the chest without skin contact. This kind of measuring without skin contact, in other words measuring carried out in practice over the clothing, simplifies and speeds up the fitting of the measuring band considerably, which has a major importance considering the use of the apparatus of the invention, for instance, in various situations of emergency.

Since vital functions can be monitored on a long-term basis by means of the apparatus of the invention, it is particularly well suited, in conjunction with diagnosing coughs of different types as well as asthma and similar respiratory diseases, for collecting and processing data in such a manner that the diagnosis of a disease can be effected on the basis of this data. Various sleeping disorders, such as apnea and snoring, can be readily detected.

In accordance with a second embodiment of the invention, the sensor arrangement is arranged to react to pressure inside a seat or bed cushion to be placed under the user. In this way the patient's vital functions can also be monitored on the basis of mechanical vibrations emanating from the patient into the cushion, if only a sensor, sufficiently sensitive to pressure, is available. A capacitive pressure sensor based on silicon technology is well suited for this kind of pressure sensor, since it can be arranged to form a part of even a very small measuring sensor arrangement due to its miniature size.

In the above, and also in the following, the apparatus of the invention is described with a human being as a measuring object, but the invention is also fairly well suited as such for monitoring the vital functions of animals, naturally provided that the evaluation apparatus comprises processing software designed for this purpose, i.e. for the animal concerned.

DESCRIPTION OF THE DRAWINGS

In the following the apparatus of the invention will be described in greater detail with reference to the accompanying drawings, in which.

DETAILED DESCRIPTION OF THE INVENTION

Figure 1:
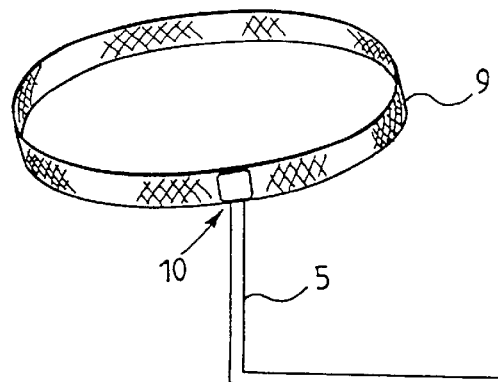
FIG. 1 is a general view of a part of the apparatus in accordance with a first embodiment of the invention.

FIG. 1 shows in principle the structure of the part of apparatus in accordance with a first embodiment of the invention, which part the person to be monitored carries about with him. It comprises, for instance, a sensor arrangement 10 to be fitted onto the user's chest, preferably at the heart, by means of a band 9 made of fabric or the like, and a data collecting device 6 connected to the sensor arrangement by means of a cable, such as a twin cable 5. At simplest, the data collecting device may be a small tape recorder, such as is used for dictation or the like. By means of a tape recorder like this a signal spectrum generated by the sensor arrangement 10 can be recorded on a magnetic tape. A preferred embodiment of the sensor arrangement 10 will be described in greater detail later on in connection with FIGS. 5 to 8. The fabric band 9 is either disposable or disinfectable and comprises an appropriate pocket or the like for the sensor arrangement 10. The data collecting device 6 for its part is provided with appropriate fixtures by means of which it can be secured, for example, to the user's belt or the like.

Figure 2:
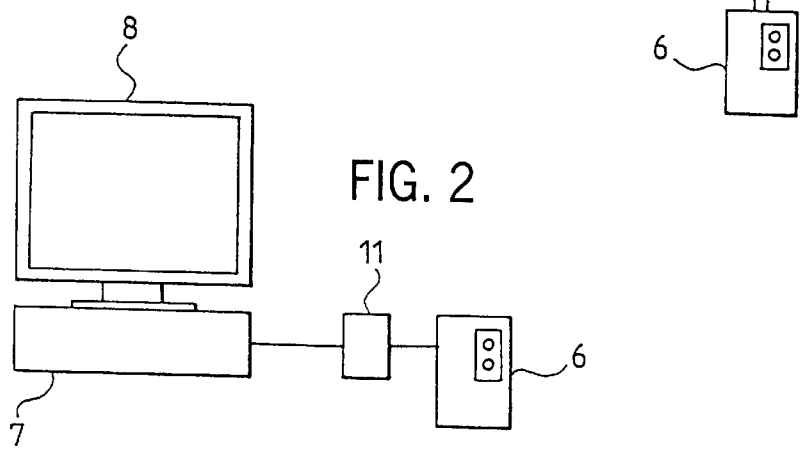
FIG. 2 is a general view of another part of the apparatus in accordance with the first embodiment of the invention.

FIG. 2 shows another part, i.e. a data processing part, of the apparatus in accordance with a second embodiment of the invention, by means of which part the information collected by the data collecting device 6 can be processed in such a way that it allows desired diagnoses. For this purpose the information collected by the data collecting device is first delivered to a unit 11 where it is edited into digital bits, whereafter it can be fed into a computer 7, such as a personal computer, to which a display unit 8 is also connected. Naturally, the unit 11 is not needed if the analog-to-digital conversion is already carried out in the sensor arrangement 10. The graphs and measured values displayed with the display unit can naturally be written out with a printer (not described) as well. Instead of the display unit 8 and the printer. a graphic plotter could also be used as an output device.

If the analog data collecting method of FIG. 1 is used, the information collected by the data collecting device 6 is in the form of an analogous oscillation spectrum in which various movements and vibrations of the user's chest are superimposed on top of each other. Both vibrations caused by respiration and vibrations caused by function of the heart can be detected therefrom. Likewise, various lung movements as well as functions of the user, such as sitting down, lying down, speaking, etc, appear therefrom, as wili be described later on in connection with FIG. 5. This kind of analog signal spectrum can be generated by means of just one sensor, such as a capacitive acceleration transducer, but it is also possible to use separate sensors for monitoring different functions. In addition to the acceleration transducer, and particularly the capacitive acceleration transducer, a strain-gage sensor, a piezoelectric power transducer, an EMF diaphragm sensor and also a pressure sensor, particularly of microcircuit type, can be used as the sensors. With these sensors each desired function can be determined as a separate signal, which signals are combined directly with each other or formed into a time-division signal spectrum, which comprises the signal spectra of different sensors as repetitive sequential short sections either in analog or digital form.

Suitable processing software for analyzing the oscillation spectrum collected by the data collecting device 6 is stored in the computer 7. By means of the software, utilizing suitable mathematical filter functions, the signal spectra originating from different physiological functions can be separated from one another.

Figure 3:
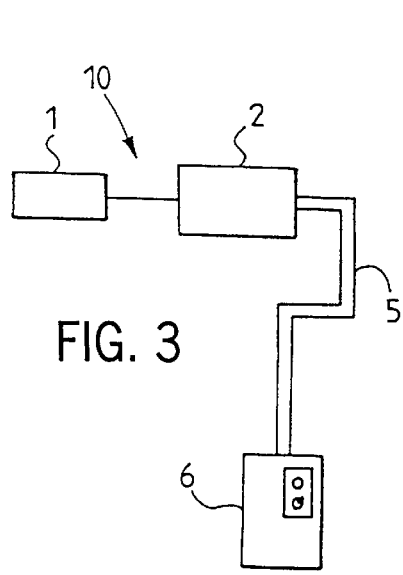
FIG. 3 is a schematic view of the structure of a first exemplary embodiment of the part of the apparatus in accordance with the first embodiment of the invention.

FIG. 3 is a structural diagram of a part of the apparatus as shown in FIG. 1. Here the sensor arrangement 10 comprises a capacitive acceleration transducer 1 and a conversion circuit 2 related thereto, by means of which changes in capacitance of the capacitive acceleration transducer 1 are converted into a voltage signal. These kinds of hybrid circuits incorporating both a capacitive acceleration transducer and a conversion circuit, implemented as an ASIC circuit, are manufactured in Finland by VTI-Hamlin Oy (for instance for active suspension of cars). Since a commercially available product is concerned, its structure is not described in greater detail herein.

On the other hand, the voltage signal received from the conversion circuit 2 can be transferred as such or amplified by means of an amplifier (not shown) via the twin cable 5 to the data collecting device 6. As stated above, a DAT-recorder or an analog tape recorder, such as a dictation recorder or the like, that are fairly well suited for recording an analog voltage signal, can be used as the data collecting device. More developed data collecting devices, which record information over a long period of time, can naturally be used as well. These kinds of data collecting devices, also for recording signals of physiological origin, are generally available.

Figure 4:
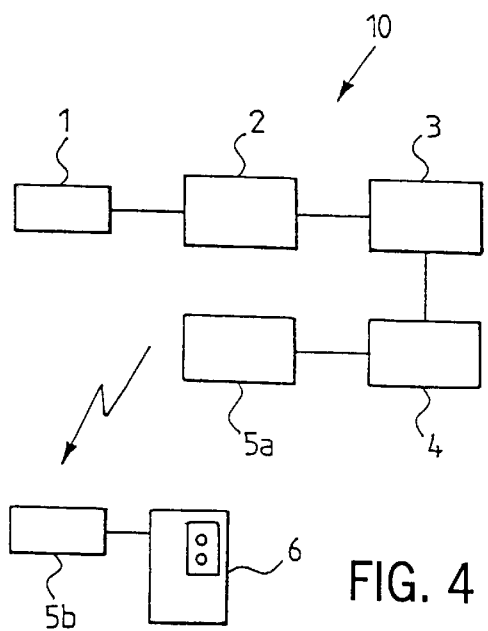
FIG. 4 is a schematic view of the structure of a second exemplary embodiment of the part of the apparatus in accordance with the first embodiment of the invention.

FIG. 4 shows an alternative structural diagram of a part corresponding to the part in FIG. 3 of the apparatus in accordance with the first embodiment of the invention. In the embodiment of FIG. 4, the sensor arrangement 10 comprises a capacitive acceleration transducer 1, a conversion circuit 2 for converting changes in capacitance of the sensor into a voltage signal, an analog-to-digital converter 3, a memory circuit 4 and a transmitter unit 5a. The analog-to-digital converter 3 converts the voltage signals of the conversion circuit 2 into a digital signal. From the analog-to-digital converter 3 the signals are transferred to the memory circuit 4 where the digitized signal spectrum can be temporarily stored. From the memory circuit 4 the information can be delivered, at convenient intervals, to the transmitter unit 5a by which the signal is transmitted to a receiver unit 5b which is arranged in connection with the data collecting device 6.

The transmitter 5a and the receiver 5b may operate at radio frequency, but data transmission by means of a magnetic field offers a simpler alternative, whereby the transmitter 5a and the receiver 5b are inductively coupled during the data transmission.

The coupling of FIG. 4 can readily be modified also in such a way that the analog-to-digital converter 3 and the memory circuit 4 are omitted, in which case the voltage signal generated by the conversion circuit 2 is transmitted directly with the transmitter 5a to the receiver 5b. As a consequence, this comes close to the analog coupling of FIG. 3, but in this case the cable connection 5 is replaced with a wireless connection. Another option would be to modify the embodiment of FIG. 4 in such a way that the signals from the analog-to-digital converter 3 would be transferred directly to the transmitter 5a. In these modifications the transmitter 5a would have to operate constantly, which can be avoided by using the memory unit 4. If the memory unit 4 is used, the operation of the transmitter 5a can be effected in bursts, i.e. the transmitter sends a signal in cycles only. In this way its energy consumption can be decreased.

The sensor arrangement 10 also comprises, for its various functions, a power source, such as an accumulator. However, in order that the measuring sensor apparatus 10 could be hermetically sealed, an option is that the accumulator within the apparatus 10 would be charged inductively. Naturally, detachable accumulators or batteries can also be used, if it is not considered necessary to seal the sensor device hermetically, for instance, by encasing it in plastic.

Figure 5:
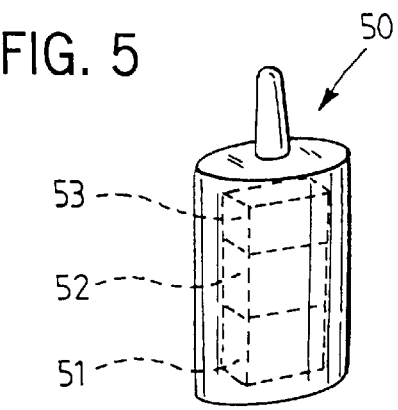
FIGS. 5 to 7 show parts of a sensor arrangement applicable to the apparatus of FIG. 1.
Figure 6:
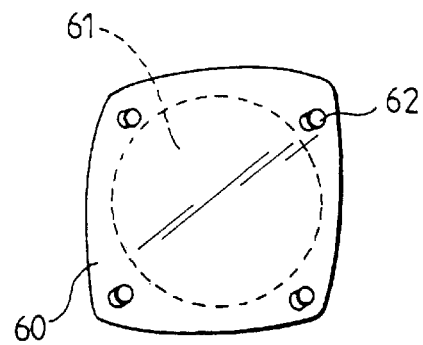
Figure 7:
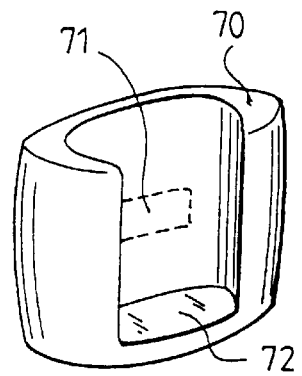
Figure 8:
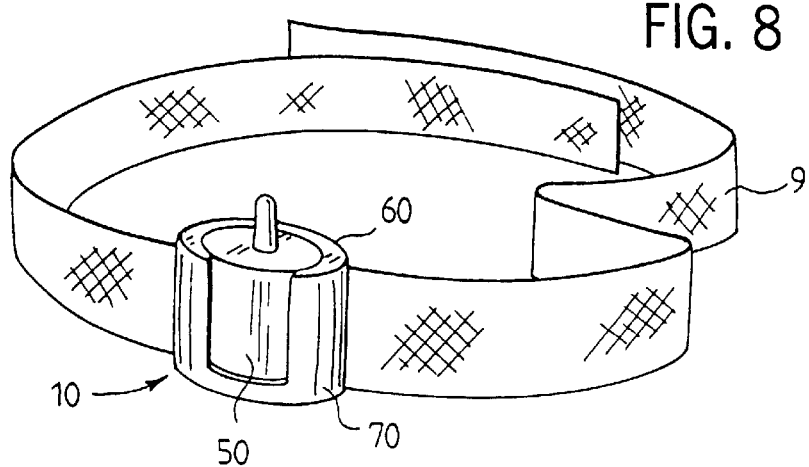
FIG. 8 shows the parts of FIGS. 5 to 7 connected to one another.

FIGS. 5 to 8 show a preferred embodiment of the sensor arrangement 10 and the band 9, to which the sensor arrangement is secured in use. FIGS. 5 to 7 show the parts that constitute the sensor arrangement. FIG. 6 shows a background part 60 which is to be connected to the band 9 in accordance with FIG. 8 on the user's side of the band. This background part 60 comprises, on the surface closest to the user, an EMF diaphragm sensor 61, which is particularly well suited for monitoring the user's heart beat and respiration. The background part is also provided with studs 62 by means of which it is connected to a front part 70 shown in FIG. 7 in such a way that the elastic portion of the band, the band comprising both a fabric-type portion and an elastic portion, is arranged between the parts 60 and 70 before the parts are connected. For this purpose, said elastic portion of the band is provided with holes for studs 62. The front part 70, on the side against the band, comprises a strain-gage sensor 71 capable of reacting to the traction power transmitted thereto through the band 9, and consequently, capable of reacting to the expansion and contraction of the user's chest, i.e. primarily to respiration. As appears from FIG. 7, the front part comprises a pocket-like recess into which the part of the sensor arrangement in accordance with FIG. 5 is to be mounted, as shown in FIG. 8. The part, shown in FIG. 5, of the sensor arrangement comprises an accumulator 51, an acceleration transducer 52 and a radio transmitter 53. Primarily, by means of the acceleration transducer 52 the user's position and movements in general are measured.

As described in the above, the sensor arrangement comprises an EMF diaphragm sensor 61, on the chest side of the part fitted onto the user's chest, and the sensor arrangement is arranged to the elastic portion of the band fitted onto the user's chest. It is important that the part of the sensor arrangement 70 comprising the strain-gage sensor 71 is arranged to be secured to the elastic portion of the band at least at two points, in the longitudinal direction of the band, on the opposite sides of the strain-gage sensor, so that the traction power affecting the band can reliably stretch the strain-gage sensor.

It is also essential that the part 60 of the sensor arrangement comprising the EMF diaphragm sensor 61 and the part 70 comprising the strain gage sensor 71 are connected to one another in such a way that the elastic portion of the band is arranged to go through between them, whereby the desired signals can be transferred to the sensors in the most efficient manner possible.

When the parts 50, 60 and 70 of the sensor arrangement are connected to one another, the sensors 61 and 71 are coupled to the electronic circuitry and accumulator 51 of the part 50 by means of a connector 72 on the bottom of the pocket of the part 70 and a matching connector on the bottom of the part 50. By means of a radio transmitter 53 the signals collected with the sensor arrangement are transmitted forwards, as described in the above in connection with FIGS. 1 to 4. The sensor arrangement structure as described in the above results primarily from the fact that a part of it, i.e. the band and the parts 60 and 70 in direct contact therewith, can be implemented with good reason patient-specifically, i.e. they can be readily discarded, whereas the part 50 incorporating more expensive components can be used several times. Consequently, the part 50 is to be implemented substantially sealed and disinfectable.

Figure 9:
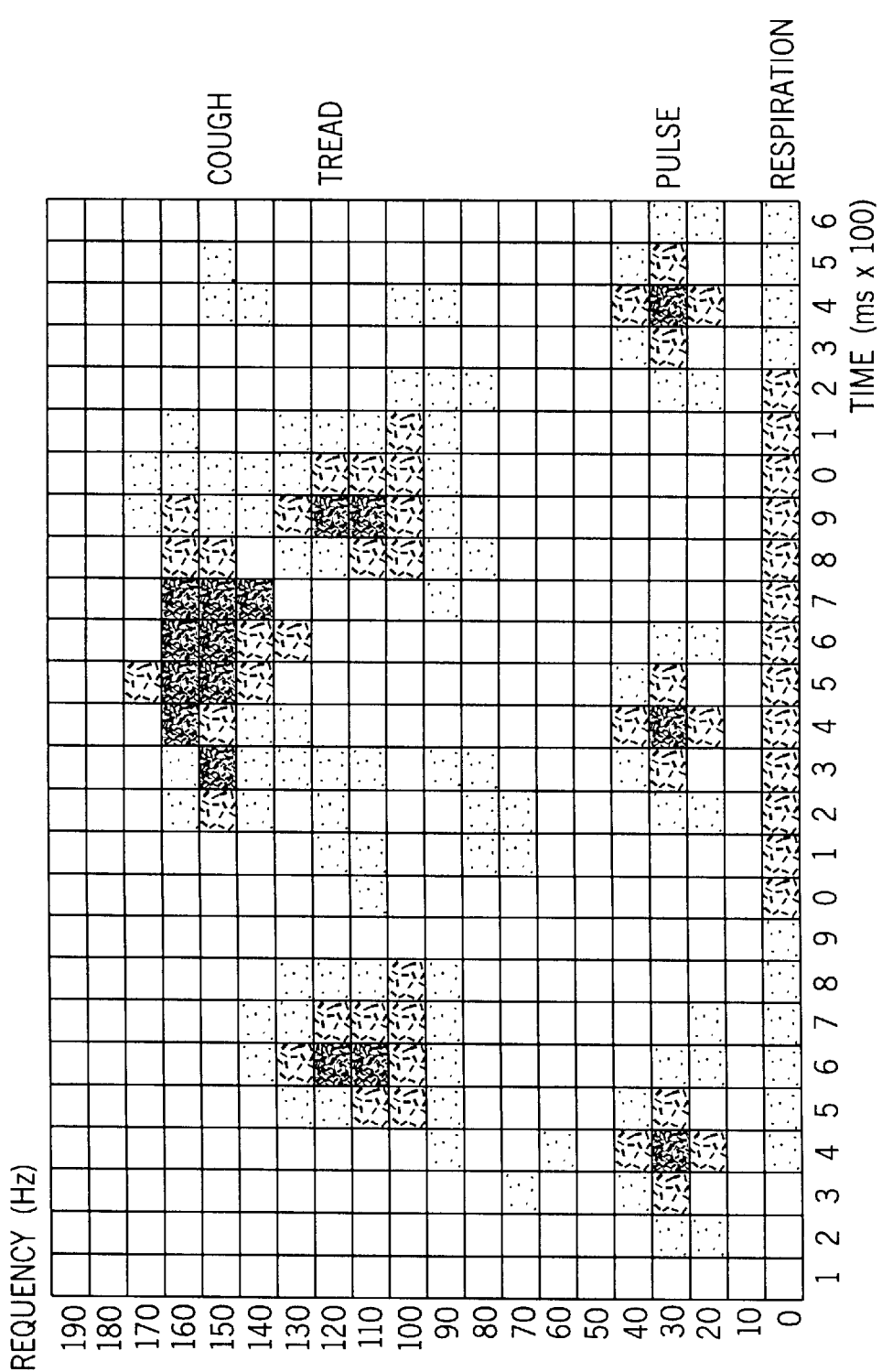
FIG. 9 illustrates an example of a composite signal spectrum as a three-dimensional model determined by means of the apparatus of the invention.

FIG. 9 shows an example in principle of a combined signal spectrum produced by means of the apparatus of the invention. In the example, information on the vital functions and body movements of a human being has been received from the sensor arrangement, and by analysing this signal from the sensor arrangement, it can be presented by means of amplitude and frequency values relating to one another as in FIG. 9. If these values are collected constantly or at successive moments, the time dimension can be combined to these values, and a three-dimensional model, such as the one in FIG. 9, is achieved. In that figure, the horizontal axis represents time, the vertical axis frequency and the depth dimension represents amplitude. In FIG. 9, the amplitude value is illustrated with the grey scale so that the darker the area of the frequency-time level the greater the amplitude relating to this area.

The functions appearing in the spectrum are mentioned in the right margin of FIG. 9. Respiration, having the lowest frequency, appears quite at the bottom of the figure, and the heart beat appears in the frequency range of 20 to 40 Hz. The frequencies of about 90 to 140 Hz show the person's walk or tread signals, and in the frequency range of about 130 to 170 Hz appears a cough signal. The combined signal spectrum of FIG. 9 can be divided into partial spectra, which means that a particular frequency range is separated from the combined spectrum of FIG. 9. Hence the signals generated, for instance, by respiration (FIG. 11) and heart beat (FIG. 12) can be separated from other signals appearing in FIG. 9.

Figure 10:
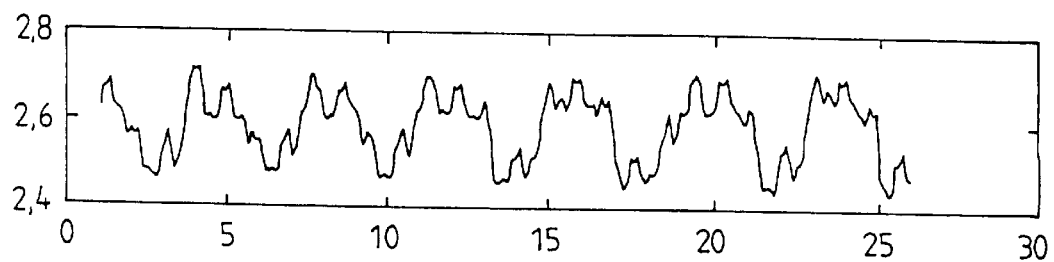
FIG. 10 illustrates part of the composite spectrum of FIG. 9 as a two-dimensional representation.
Figure 11:
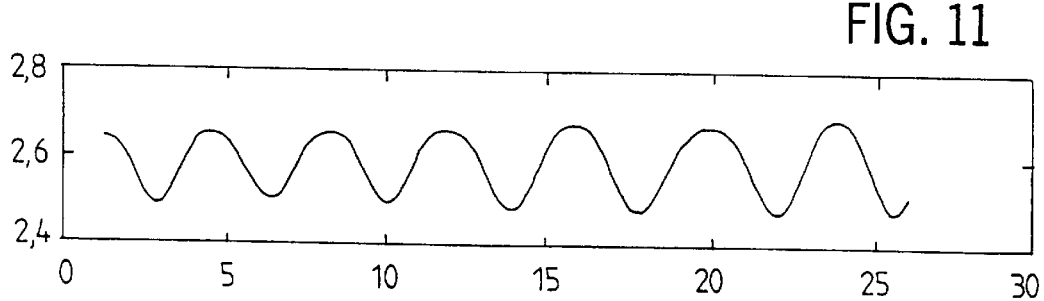
FIG. 11 illustrates a respiratory signal filtered from the spectrum of FIG. 9.
Figure 12:
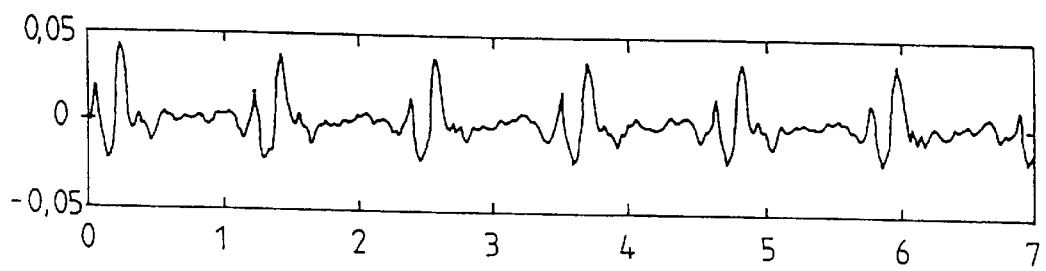
FIG. 12 illustrates a pulse signal filtered from the spectrum of FIG. 9.

FIG. 10 shows an example of a signal that is obtained when a frequency range of about 0 to 50 Hz is separated from the spectrum of FIG. 9 and represented two-dimensionally on the amplitude-time scale. This signal comprises portions generated by respiration and function of the heart alike. FIG. 11 shows a respiration signal obtained by filtering it from the signal of FIG. 10, and FIG. 12 shows a pulse signal obtained by filtering it from FIG. 10 as well. It must be mentioned that the example in FIGS. 10 to 12 is based on substantially smaller screen ruling than in FIG. 9. Thus the graphs in FIGS. 10 to 12 have no grades, which would be the case if the screen ruling were the same as in FIG. 9.

Figure 13:
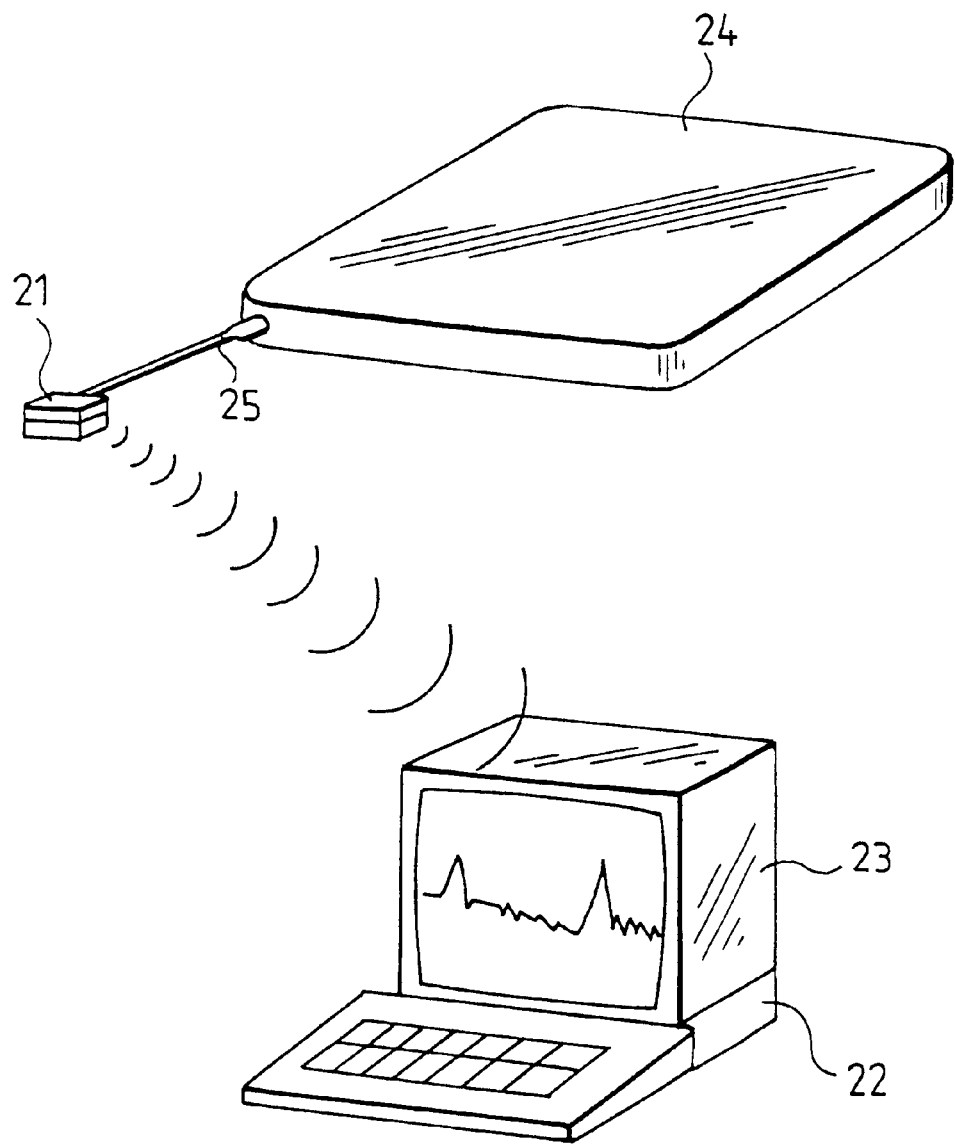
FIG. 13 is a general view of a part of the apparatus in accordance with a second embodiment of the invention.

FIG. 13 shows a schematic view of a part of the apparatus in accordance with the second embodiment of the invention. The apparatus shown in the figure comprises a cushion 24 and a sensor arrangement 21 arranged to measure the interior pressure of the cushion, the sensor arrangement comprising a sensor responsive to pressure, means for processing the signal, generated by the sensor, in an appropriate manner, and transmission means, such as an ultrasound transmitter, for transmitting the signal generated by the sensor arrangement to a storing and processing apparatus, such as a computer 22, which may be a general-purpose personal computer provided with convenient software. The signal analysis performed by the computer 22 can be displayed, for instance, on the computer screen 23 or with some other convenient display or output device.

The cushion 24 may be a pad, intended for use under a sitting patient, or a mattress, intended for use under a lying patient. The cushion 24 is filled with fluid medium, i.e. liquid, gas or fluid gel containing considerably air or some other gaseous medium. This cushion 24, or in fact, its interior is connected with a hose 25 to the sensor arrangement 21. A sensor reacting to the interior pressure of the cushion 24 is arranged to this sensor arrangement 21. Most preferably the sensor is an extremely sensitive, capacitive, miniature pressure sensor based on silicon technology. Capacitive pressure sensors like this are manufactured in Finland by VTl-Hamlin Oy.

When sitting down or lying down on the cushion, the patient causes a change in the interior pressure of the cushion 24. This change correlates directly with the person's weight. Naturally, when the person moves on the cushion, it also causes momentary changes in the interior pressure of the cushion, and they can be recorded by means of the pressure sensor. The patient's respiration also appears as changes in the interior pressure of the cushion, as does the recoil caused by heart beat. Even though the changes in pressure caused by respiration and heart beat are minor, the above-described pressure sensor is capable of recording them. Moreover, if a capacitive thermistor is connected to the cushion, the patient's body temperature can also be recorded.

In accordance with the above, in the embodiment of FIG. 13 the signal generated by the sensor arrangement, incorporating a pressure sensor and an eventual thermistor, can be processed and analyzed exactly in the same manner as was previously described in connection with FIGS. 1 to 12. Thus FIG. 13 does not show in greater detail various device combinations and possibilities that are available for processing the signal generated by the sensor arrangement, since these possibilities have already been referred to in connection with the embodiments of FIGS. 1 to 12.

In the above, the apparatus of the invention has only been described with reference to some exemplary embodiments, so it is obvious that they can be modified to some extent within the scope determined by the appended claims.

What is claimed is:

1. An apparatus for monitoring mechanically transmitted physiological phenomena based on the organs or vital functions of a subject and for processing the monitoring results, the apparatus comprising:

a measuring sensor arrangement (10) adapted to be placed on the subject, said measuring sensor arrangement comprising at least two measuring sensors (1, 52, 61, 71) responsive to the mechanically transmitted physiological phenomena and signal processing means (2:2, 3, 4) for processing sensor signals, transmission means (5; 5a, 5b,) for transmitting a signal generated by the measuring sensor arrangement (10), a data collecting device (6) for receiving and storing the signal transmitted by the transmission means, means (7) for processing the signal stored by the data collecting device (6), and a display or output device (8) for presenting the results of processing, wherein said at least two measuring sensors of the measuring sensor arrangement (10) are each of a different sensor type, each of said sensors being responsive to a physiological phenomenon that another one of said sensors is also responsive to, at least one of said sensors being responsive to an additional physiological phenomenon, said measuring sensor arrangement being arranged to produce a single, unmodulated, composite spectrum signal based on a plurality of vital functions and containing spectral signals produced by said measuring sensors of different types, and wherein the means (7) for processing data, stored by the data collecting device, comprise processing software for dividing the unmodulated, composite spectrum signal generated by the measuring sensor arrangement into a plurality of partial spectrum signals of different physiological origins.

2. An apparatus as claimed in claim 1, characterized in that the means (7) for processing the signal stored by the data collecting device (6) comprise a general-purpose personal computer.

3. An apparatus as claimed in claim 1, characterized in that the measuring sensor arrangement (10, 21) is arranged to generate the signal based on the functions of heart and lungs, and body movements.

4. An apparatus as claimed in claim 1, characterized in that the sensor arrangement (10) is arranged to be fitted onto the subject's chest without skin contact.

5. An apparatus as claimed in claim 1, characterized in that the sensor arrangement (10) comprises measuring sensors selected from the following sensor types: capacitive acceleration transducer (1, 52), EMF diaphragm sensor (61) and strain-gage sensor (71).

6. An apparatus as claimed in claim 5, characterized in that the sensor arrangement (10) comprises one sensor of each said sensor type.

7. An apparatus as claimed in claim 1, characterized in that the sensor arrangement includes an EMF diaphragm sensor (61) on the chest side of a part fitted onto the subject's chest.

8. An apparatus as claimed in claim 1, characterized in that the sensor arrangement is arranged in an elastic portion of a band fitted onto the subject's chest.

9. An apparatus as claimed in claim 8, characterized in that the sensor arrangement (70) includes a strain-gage sensor (71) arranged to be secured in the elastic portion of the band at at least two points, spaced in a longitudinal direction of the band, said points being located on opposite sides of the strain-gage sensor.

10. An apparatus as claimed in claim 8, characterized in that a part (60) of the sensor arrangement comprising an EMF diaphragm sensor (61) and a part (70) of the sensor arrangement comprising a strain-gage sensor (71) are connected to one another in such a way that the elastic portion of the band is arranged to extend between them.

11. An apparatus as claimed in claim 9, characterized in that part (70) of sensor arrangement comprising the strain-gage sensor (71) comprises a pocket-like recess for the part

(50) of the sensor arrangement incorporating a transmitter (53), an acceleration transducer (52) and an accumulator (51).

12. An apparatus as claimed in claim 1, characterized in that the single, composite spectrum signal generated by the sensor arrangement (10) comprises superimposed signals produced by said measuring sensors.

13. An apparatus as claimed in claim 1, characterized in that the composite spectrum signal generated by the sensor arrangement (10) comprises the signals generated by said measuring sensors as a time-division signal formed by the signals of said measuring sensors.

14. An apparatus as claimed in claim 1, characterized in that the transmission means for transmitting the composite signal generated by the sensor arrangement (10) comprise a transmitter (5a) arranged in conjunction with the sensor arrangement (10) and a receiver (5b) arranged in conjunction with the data collecting device (6).

15. An apparatus as claimed in claim 14, characterized in that the transmitter comprises an ultrasound transmitter and the receiver comprises a microphone.

* * * * *